United States Patent [19]

LaMarco et al.

[11] Patent Number: 5,635,349
[45] Date of Patent: Jun. 3, 1997

[54] HIGH-THROUGHPUT SCREENING ASSAY FOR INHIBITORS OF NUCLEIC ACID POLYMERASES

[75] Inventors: Kelly LaMarco; Berta Strulovici; Pengguang Wu, all of San Francisco, Calif.

[73] Assignee: Tularik, Inc., San Francisco, Calif.

[21] Appl. No.: 348,797

[22] Filed: Dec. 2, 1994

[51] Int. Cl.[6] .................. C12Q 1/68; C12Q 1/70; C12P 19/34; C07H 21/04

[52] U.S. Cl. .................. 435/6; 435/5; 435/91.2; 536/24.3; 623/6; 422/101; 210/633

[58] Field of Search .................. 623/6; 422/101; 210/633; 435/6, 5, 91.2; 536/24.3

[56] References Cited

FOREIGN PATENT DOCUMENTS 0281390  9/1988  European Pat. Off. .

OTHER PUBLICATIONS

Flanagan et al., "Simple Derivation of TFIID–dependent RNA polymerase II Transcription Systems from *Schizosaccharomyces pombe* and Other Organisms, and Factors Required for Transcriptional Activation", *Proc. Natl. Acad. Sci. USA* 89:7659–7663 (1992).

Ruet et al., "A Specific Assay for Yeast RNA polymerases in Crude Cell Extracts", *Eur. J. Biochem.* 90:325–330 (1978).

Sorger et al., "Identification and Purification of Sequence-specific DNA–binding Proteins", *Protein Function—A Practical Approach* Creighton, Ed. IRL Press, Oxford University Press, Oxford, NY (1989).

Stunnenberg et al., "RNA Polymerase from the Fungus *Aspergillus nidulans*", *Eur. J. Biochem.* 98:107–119 (1979).

*Primary Examiner*—W. Gary Jones
*Assistant Examiner*—Dianne Rees
*Attorney, Agent, or Firm*—Flehr, Hohbach, Test, Albritton & Herbert

[57] ABSTRACT

The invention provides promoter specific and promoter non-specific screening assays for identifying an inhibitor of a pathogenic nucleic acid polymerase activity, e.g. an RNA polymerase derived from a pathogenic infectious organism such as a bacterium, protozoan or fungus. Generally, the methods involve forming a mixture of nucleotides, a polynucleotide template, a pathogenic polymerase candidate inhibitor of polymerase activity, where at least one of the nucleotides comprises a detectable label. The mixture is incubated under conditions whereby, but for the presence of the candidate inhibitor, the polymerase transcribes the polynucleotide template by catalyzing the polymerization of the nucleoside triphosphates into a polynucleotide having a nucleotide sequence complementary to that of the polynucleotide template. The nascent transcript is captured by a polynucleotide-selective agent immobilized on a solid substrate for subsequent washing and label detection.

7 Claims, 1 Drawing Sheet

HIGH-THROUGHPUT SCREENING ASSAY FOR INHIBITORS OF NUCLEIC ACID POLYMERASES

INTRODUCTION

1. Field of the Invention

The field of this invention is assays for screening for inhibitors of a certain class of enzymes, namely nucleic acid polymerases.

2. Background

Specific enzyme inhibitors find a wide range of applications in the food and agriculture industries, the medical, pharmaceutical and biotechnology industries, etc. These fields in particular provide numerous commercial applications for effective inhibitors of nucleic acid polymerases. Specific nucleic acid polymerase inhibitors would find application in agricultural and live stock pest control, in industrial and academic biomedical research and development programs, and in clinical settings. For examples, domestic grain storage facilities suffer tremendous losses to fungal infestation without effective protective or remedial treatments; biomedical researches are compelled to spend time and resources purifying away contaminating polymerase activity for want of an effective and specific polymerase inhibitor; and clinicians face an ever increasing number of pathogens resistant to existing antibiotics.

Available inhibitors of nucleic acid polymerases are very limited. The antibiotic drug rifampin is believed to selectively inhibit certain bacterial RNA polymerases and $\alpha$-amanatin is believed to selectively inhibit certain eukaryotic RNA polymerases. $\alpha$-Amanatin demonstrates that polymerase inhibitors can be quite specific: despite conservation between eukaryotic polymerases, yeast RNA pol II is 10- to 100-fold less sensitive to $\alpha$-amanatin than is mammalian RNA pol II, probably as a result of an asparagine to serine substitution at residue 793 of the largest RNA polymerase subunit.

Relevant Literature

Polymerase assays are reported in Ruet et al (1978) Eur J Biochem 90, 325–330.

RNA polymerase purification procedures are reported in Sorger et at. in Protein Function—A Practical Approach. Creighton, Ed. IRL Press, Oxford Univ Press, Oxford, N.Y., 1989 and Sentenac, A. (1985), in CRC Critical Reviews in Biochemistry, 18, 31–91.

Partial purifications of specific fungal RNA polymerase II's are reported in Flanagan et al (1992), PNAS 89, 7659–7663 (*S. cereviseae*) and in Stunnenberg, et al (1979) Eur J Biochem 98, 017–119 (*Aspergillus nidulans*).

SUMMARY OF THE INVENTION

The invention provides methods and compositions for identifying an inhibitor of a pathogenic nucleic acid polymerase activity, e.g. an RNA polymerase derived from a pathogenic infectious organism such as a bacterium, protozoan or fungus. The invention provides both promoter specific and promoter non-specific inhibitor screening assays.

In general, the methods involve forming a mixture by combining nucleotides, a polynucleotide template, a pathogenic nucleic acid polymerase and a candidate inhibitor of the targeted nucleic acid polymerase activity, where at least one of the nucleotides comprises a detectable label. The mixture is incubated under conditions whereby, but for the presence of the candidate inhibitor, the nucleic acid polymerase transcribes the polynucleotide template by catalyzing the polymerization of the nucleoside triphosphates into a polynucleotide having a nucleotide sequence complementary to that of the polynucleotide template. The incubated mixture is contacted with and incubated in the presence of a polynucleotide-selective agent immobilized on a solid substrate, under conditions to selectively bind the polynucleotide to the polynucleotide-selective agent. Thereafter, the solid substrate is separated from the mixture and washed substantially free of free nucleotides. The presence or absence of the detectable label on the solid substrate is then detected, where the absence (or aggregate reduction) of the label on said solid substrate indicates that the candidate inhibitor of nucleic acid polymerase activity is an inhibitor of a pathogenic nucleic acid polymerase activity.

According to a preferred embodiment, the polynucleotide-specific agent immobilized on a solid substrate is a suspension of diethylaminoethyl polymeric microbeads, the separating step is performed by vacuum-assisted filtration, and the incubation, separation and washing steps are practiced in a membrane filtration apparatus comprising a tube, such as a well of a microtiter plate, having a fluid passage comprising a reservoir portion, a first filter and a second filter, each filter extending transversely across the passage, with the first filter positioned between the reservoir portion of the passage and the second filter. The first filter is initially hydrophobic and capable of retaining liquid media for extended incubations (e.g. 1 hr.) and is rendered water-permeable by contacting it with an organic solvent. The second filter is hydrophilic water-permeable, has a maximum pore size less than about 200 um diameter and is capable of substantially retaining liquid media under short incubations (e.g. 1 min) under atmospheric pressure while efficiently passing liquid media while retaining microbeads during vacuum filtration. To facilitate high-throughput application of the method, the forming step, separating step and washing step are preferably performed in a microliter plate by a computer-controlled electromechanical robot comprising an axial rotatable arm.

DETAILED DESCRIPTION OF THE INVENTION

Figure 1:
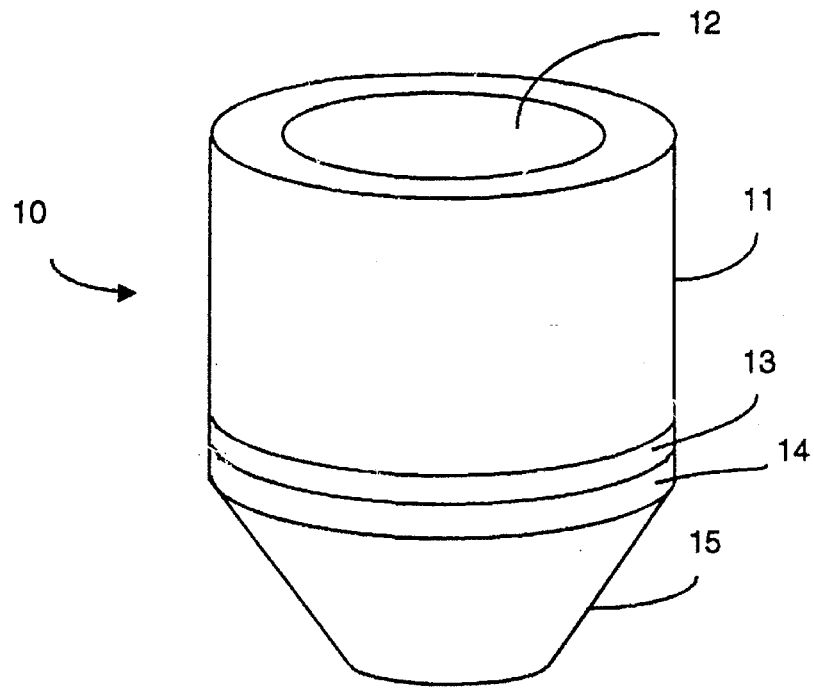
FIG. 1 shows a side-view of a representative well of a membrane-filtration microtiter plate—drip director combination having the preferred dual-membrane filters pressure-sealed between the hermetically sealed tube and drip-director plates.

The invention provides high-throughput methods and compositions for identifying a specific inhibitor of a pathogenic nucleic acid polymerase activity. Polymerase activity is detected as the ordered polymerization of nucleoside triphosphates to form a polynucleotide transcript from a polynucleotide template. Depending upon the construction of the assay, inhibition can occur at one or more of a number of transcriptional points including initiation, elongation and termination. Hence, the detected polymerase activity may result from one or a number of transcriptional components providing numerous inhibitor target sites. For example, promoter nonspecific assays where the selected polymerase initiates transcription at single-stranded regions and nicks in a template are used to identify inhibitors of transcript elongation and hence, the polymerase per se. Alternatively, promoter specific assays using a double-stranded template with a predetermined transcription regulatory sequence, are used to target for inhibition one of a plurality of transcriptional components involved in transcriptional initiation, elongation and termination. Promoter-nonspecific assays are conveniently applied to either eukaryotic or prokaryotic transcription systems. Promoter-specific assays are exemplified with prokaryotic polymerases where the label incorporation is found to be more suitable the for application of the preferred transcript capture, wash and filtration techniques and the disclosed the high-throughput methods.

Inhibitor specificity is ensured by exploiting differences between the pathogenic and non-pathogenic host polymerases. For example, the antibiotic drug rifampin selectively inhibits bacterial RNA polymerases and yeast RNA pol II is 10- to 100-fold less sensitive to α-amanatin than is mammalian RNA pol II. Hence, inhibitors effective against a foreign pathogenic polymerase are conveniently screened for diminished activity against mammalian, preferably human polymerases. Candidate agents shown to specifically inhibit pathogenic polymerase activity provide valuable reagents to the pharmaceutical and agricultural industries as biochemical reagents for a wide variety of in vitro and cellular applications, in plant and field crops, pesticides, fungicides, particularly broad-spectrum fungicides, etc. applications, in animal and human trials for diagnostic and therapeutic applications, etc. The biomedical research industry and academia provide many other applications of specific polymerase inhibitors. For examples, specific inhibitors would free technicians from laborious and expensive polymerase purifications, could be used to determine the specific polymerase involved in the transcription of a gene under investigation, and could be used in a wide variety of in vitro transcription systems.

The general polymerase assay methods involve forming a mixture of nucleoside triphosphate with at least a polynucleotide template, a pathogenic polymerase and a candidate inhibitor of polymerase activity. Usually, all four of nucleotides are provided together, e.g. in the case of the preferred RNA polymerase assays: adenosine triphosphate, guanosine triphosphate, cytidine triphosphate and uridine triphosphate together. A notable exception to the usual use of all four nucleotides is assays using a template devoid of a particular nucleotide to insure transcript specificity. For example, if a G-less cassette/template is used in the absence of guanosine triphosphate, the generation of transcripts other than of the template is minimized. Nucleotide analogs may be substituted so long as they are amenable to sequence-specific polymerization by the targeted polymerase activity. In a preferred embodiment, at least one of the nucleoside triphosphates comprises a detectable label, particularly a radiolabel such as an radioactive phosphorous atom incorporated into a phosphate group. The nucleoside triphosphates are preferably provided in amounts which exceed the Km of the polymerase and are non-limiting under assay conditions. Typically, the concentration ranges from 1 uM to 1 mM. An exception is labeled or "hot" nucleotide (e.g. $^{32}$P-CTP) which is often provided at a lower concentration (e.g. 100 to 500-fold less than the other nucleotides) to maximize incorporation of label.

The polynucleotide template may be in any form capable of yielding a detectable transcript in the subject methods. For example, in promoter non-specific methods, the template may be any of a variety of convenient single-stranded nucleic acid sources, usually DNA. Exemplary sources are low cost and readily available and include calf thymus and salmon sperm DNA and plasmid DNA. Single stranded DNA is readily prepared by heat-denaturing and nicked DNA is readily prepared (e.g. from plasmid DNA) with restriction enzymes. For promoter specific embodiments, the template is usually a defined double-stranded construct comprising predetermined transcription regulatory and initiation sequences, amplified by means such as the PCR or replication in an appropriate plasmid. Generally, the transcribed template is a portion of a larger nucleic acid; for promoter specific assays, the nucleic acid is usually supercoiled. Template size is a matter of convenience so long as the transcript is long enough to be efficiently distinguished from free nucleotides in the subsequent capture and wash steps and short enough to avoid shearing or secondary structure sufficient to interfere with transcription or the subsequent capture, wash or counting steps.

The pathogenic polymerase has functional and sequence similarity, preferably sequence identity, with a polymerase of an pathogenic infectious organism such as a bacterium, protozoan or fungus. For therapeutic and diagnostic applications, RNA polymerases specific to disease causing microorganisms, particularly fungi, provide especially important and preferred inhibitor targets. RNA polymerases are large, multisubunit enzymes providing numerous target binding sites for small molecule inhibitors, e.g. allosteric and substrate binding sites. The assays require sufficient polymerase structure to effect the targeted activity, at least transcript elongation activity and frequently one or more steps of transcriptional initiation. The polymerase and/or one or more of its subunits is preferably purified or partially purified and may be from natural or recombinant sources. The RNA polymerase may be of any class including RNA polymerase I, II or III.

Preferred pathogenic polymerases derive from medically significant infectious fungi such as Aspergillus, Candida species; bacteria such as Staphylococci (e.g. auroreus), Streptococci (e.g. pneurnoniae), Clostridia (e.g. perfringens), Neisseria (e.g. gonorrhoeae), Enterobacteriaceae (e.g. coli), Helicobacter (e.g. pylori), Vibrio (e.g. cholerae), Capylobacter (e.g. jejuni), Pseudomonas (e.g. aeruginosa), Haemophilus (e.g. influenzae), Bordetella (e.g. pertussis), Mycoplasma (e.g. pneumoniae), Ureaplasma (e.g. urealyticum), Legionella (e.g. pneumophila), Spirochetes (e.g. Treponema, Leptospira and Borrelia), Mycobacteria (e.g. tuberculosis, smegmatis), Actinomycies (e.g. (israelii), Nocardia (e.g. asteroides), Chlamydia (e.g. trachomatis), Rickettsia, Coxiella, Ehrilichia, Rochalimaea, Brucella, Yersinia, Fracisella, and Pasteurella and; protozoa such as sporozoa (e.g. Plasmodia), rhizopods (e.g. Entamoeba) and flagellates (Trypanosoma, Leishmania, Trichomonas Giardia, etc.). Another source of pathogenic polymerases are viruses d viruses that harbor or exploit a pathogenic polymerase such as (+) RNA viruses (examples include Picornaviruses, e.g. polio; Togaviruses, e.g. rubella; and Coronaviruses), (−) RNA viruses (examples include Rhabdoviruses, e.g. VSV; Paramyxoviruses, e.g. RSV; Orthomyxoviruses, e.g. influenza; Bunyaviruses and Arenaviruses), dsDNA viruses (Reoviruses, for example), RNA to DNA viruses, i.e. Retroviruses, e.g. HIV, and certain DNA to RNA viruses such as Hepatitis B viruses which contain a pathogenic DNA polymerase that completes a short viral (+) strand soon after infection. Several RNA polymerases from infectious microbes have been either purified or cloned. For example, the purification of a RNA pol II from Candida albicans is described below.

The mixture also comprises a candidate pharmacological agent. Candidate agents encompass numerous chemical classes, though typically they are organic compounds; preferably small organic compounds. Small organic compounds have a molecular weight of more than 50 yet less than about 2,500, preferably less than about 1000, more preferably, less than about 500. Candidate agents comprise functional chemical groups necessary for structural interactions with proteins and/or DNA, and typically include at least an amine, carbonyl, hydroxyl or carboxyl group, preferably at least two of said functional chemical groups, more preferably at least three. The candidate agents often comprise cyclical carbon or heterocyclic structures and/or aromatic or polyaromatic structures substituted with one or more of the forementioned functional groups.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural and synthetically produced libraries and compounds are readily modified through conventional chemical, physical, and biochemical means. In addition, known pharmacological agents may be subject to directed or random chemical modifications, such as acylation, alkylation, esterification, amidification, etc., to produce structural analogs.

Depending on the nature of the polymerase and template, the assay mixture may comprise additional transcriptional regulators and factors which associate with the target polymerase and/or template and/or auxiliary proteins or portions thereof which mediate, facilitate or otherwise enhance sequence-specific protein-nucleic acid binding. Such factors may be present in relatively crude polymerase extracts or the desired mixture may be reconstituted from exogenous sources, recombinant or separately purified. In addition, the mixture usually includes additional reagents, such as salts, buffers, etc. to facilitate maximal in vitro transcriptional activity. A variety of other reagents may also be included in the mixture. These include reagents like detergents which may be used for example, to reduce non-specific or background binding of labeled nucleotides to the solid substrate, and reagents that otherwise improve the efficiency of the assay, such as protease inhibitors, nuclease inhibitors, anti- microbial agents, etc. are often included.

The mixture is incubated in a reaction vessel or reservoir under conditions whereby, but for the presence of the candidate inhibitor, the polymerase transcribes the polynucleotide template by catalyzing the polymerization of the nucleotide triphosphates into a polynucleotide having a nucleotide sequence complementary to that of the template. A wide variety of transcription reaction conditions can be employed depending on the selected polymerase; in vitro conditions to support activity of polymerases are exemplified below and known in the art. For many polymerases pathogenic in mammals, the transcription reaction is carded out at elevated temperatures, usually in the range of 30° to 40° C., more usually in the range of 33° to 38° C. For high-throughput applications, reactions time is minimized, and is usually from 0.1 to 4 hours, more usually about 0.5 to 1.5 hours.

After transcription, the nascent transcript incorporating the label must be separated from the labeled free nucleoside triphosphate(s). A wide variety of methods may be used to separate these mixture components, e.g. exploiting size, solubility or charge density differences. For example, one may use trichloroacetic acid to precipitate labeled transcripts and then use a filtration step (e.g. vacuum assisted filtration through GFC membrane) to separate larger transcripts from unincorporated nucleotides. In another and preferred embodiment, the transcript-containing mixture is contacted with and incubated in the presence of a polynucleotide-selective agent immobilized on a solid substrate, under conditions to selectively bind (capture) the polynucleotide to the immobilized polynucleotide-selective agent. In addition, the solid substrate provides convenient means for washing the nascent transcripts. Preferred solid substrates provide maximal transcript binding sites and hence, maximal signal strength, usually by maximizing transcript-accessible surface. Hence, preferred substrate structures includes fine fibers, beads, etc. According to a preferred embodiment, polymeric (e.g. Sepharose) beads of size range and structure to maximize surface area, filter retention and bead suspension time during the assay incubations are chosen. Generally, bead diameters range from 1 to 400 um, usually from 2 to 200 um.

Selected polynucleotide-selective agents must be capable of preferentially binding the polynucleotide in the presence of at least the labelled nucleoside triphosphate(s). Preferred agents are not polynucleotide sequence-specific (e.g. nucleic acid-nucleic acid hybridization capture) but rather are polycationic and bind the transcript by non-sequence-specific polyionic bonding. Preferred agents contain amine groups positively charged under the assay incubation and wash conditions, e.g. DEAE (diethylaminoethyl) groups, QAE, lysine or polylysine. The agent is immobilized on the solid substrate, usually by covalent binding, directly or through a linking group.

The mixture containing nascent transcript is incubated in the presence of the immobilized agent for a time and under conditions to selectively bind the transcript to the substrate. Especially where the capture involves ionic binding, it is necessary to provide the mixture with a suitable pH buffer and salt to ensure the ionic strength and pH of the mixture is conducive to agent-transcript binding. For high-throughput applications, the capture incubation is generally less than 4 hours, preferably less than 2 hours, more preferably less than about 1 hour. Typically, capture is most conveniently done at room temperature. In some assays, it is possible to combine the transcription reaction and capture steps where the transcription reaction occurs in the presence of the immobilized transcript-binding agent. After capture, the solid substrate is separated from the mixture and washed substantially free of at least the labeled nucleotide and preferably all present unpolymerized nucleoside triphosphates.

Figure 2:
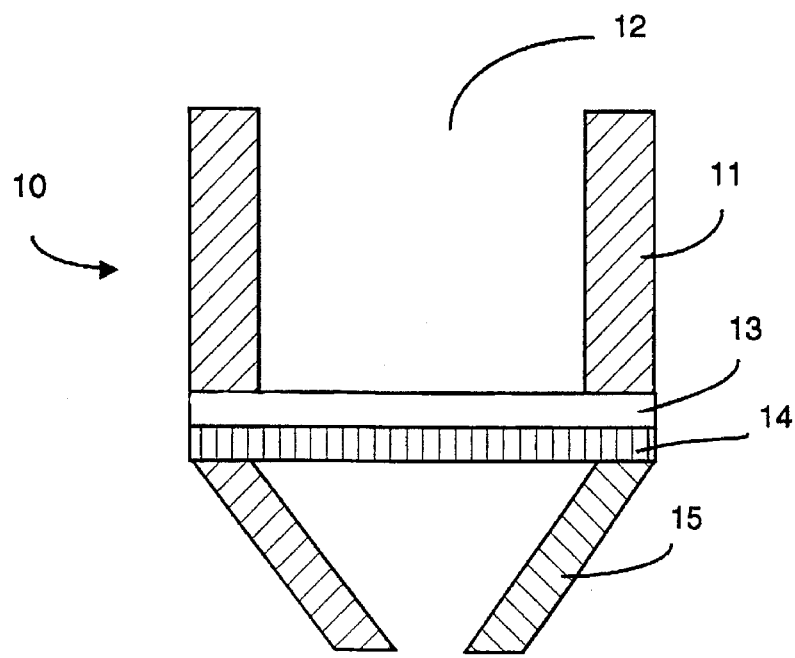
FIG. 2 shows a cross-sectional view of a representative well of the membrane-filtration microtiter plate—drip director combination shown in FIG. 1.

The method used for separating and washing will depend on the nature of the reaction reservoir and the solid substrate. For example, where the substrate is in the form of aggregated fibers, the solid phase may be physically transferred from the reaction reservoir to a series of rinse reservoirs. In a preferred embodiment, see FIG. 1 and 2, the separating and washing steps are performed by filtration, preferably vacuum-assisted filtration and the methods are practiced in a membrane filtration apparatus 10, comprising a tube 11, such as a well of a microtiter plate, having a fluid passage comprising a reservoir portion 12, a first filter 13 and a second filter 14, each filter extending transversely across the passage, with the first filter positioned between the reservoir portion of the passage and the second filter, and a drip director 15. The first filter is changeable from hydrophobic, water-impermeable to water-permeable by contacting it with an effective concentration of an organic solvent and second filter is water-permeable and has a maximum pore size less than about 200 um diameter. Typical permeablizing solvents include alcohol, particularly methanol, solutions in the 30 to 90%, usually 40 to 80%, more usually about 60% (v/v) range. The second filter is usually hydrophilic and capable of permitting the passage of at least about 90% by volume of free water from the reservoir portion of the passage while retaining at least about 90% by volume of particles with a size range of 20 to 200 um diameter in the reservoir portion of the passage. Both filters should minimize final retention of unpolymerized labeled radionucleotides under the assay conditions. Preferred filter-microtiter plate constructs demonstrate no leakage of a 50% (v/v) water/methanol solution over 1 hour under atmospheric pressure and no separation of the drip-director and no cross-talk between wells under a vacuum of 12 mm Hg. In a particularly preferred embodiment, the first filter is an MP PP hydrophobic polypropylene membrane (Polyfiltronics, Rockland, Mass.) and the second filter is a GF/C hydrophilic glass fiber membrane (Polyfiltronics, Rockland, Mass.).

After washing, the presence or absence (or aggregate reduction) of the detectable label retained on the solid substrate is then detected. A variety of methods may be used to detect the label depending on the nature of the label and other assay components. Labels may be directly detected through optical or electron density, radiative emissions, nonradiative energy transfers, etc. In the preferred case of radioactive labels, emissions may be detected directly, e.g. with particle counters or indirectly, e.g. with scintillation cocktails and counters. In a preferred embodiment, the bottom of the double-filtered filtration tube is heat-melt sealed by contacting the tube-bottom with a hot plate, scintillation cocktail is added to the reservoir, and the radiolabel present in the tube counted.

The disclosed methods are particularly suited to automated high throughput drug screening. In a preferred embodiment, the individual sample incubation volumes are less than about 500 ul, preferably less than about 250 ul, more preferably less than about 100 ul. Such small sample volumes minimize the use of often scarce candidate agent, expensive transcription complex components, and hazardous radioactive waste. Furthermore, the methods provide for automation, especially computerized automation. Accordingly, the method steps are preferably performed by a computer-controlled electromechanical robot. While individual steps may be separately automated, a preferred embodiment provides a single computer-controlled multifunction robot with a single arm axially rotating to and from a plurality of work stations performing the mixture forming, incubating and separating steps. The computer is loaded with software which provides the instructions which direct the arm and work station operations and provides input (e.g. keyboard and/or mouse) and display (e.g. monitor) means for operator interfacing.

In a particular embodiment, the robotic arm is equipped with a general purpose retrieving hand and a pipetting hand. The pipetting hand equipped with a multichannel pipettor retrieves and transfers measured aliquots of each an assay buffer, a solution comprising one or more candidate agents, a solution comprising a labeled nucleotide, a solution comprising the nucleic acid template, and a solution comprising the targeted polymerase activity into each designated well. The general purpose hand then transfers each microtiter plate to an incubator. After a first incubation period for a time and at a temperature to permit assay-detectable polymerization (e.g. 0.5 to 1.5 hours at 34° C.), the general purpose hand transfers each plate to a microbead dispensing station (e.g. a Multidrop system) which deposits in each designated well a measured aliquot of a slurry of DEAE-microbeads (e.g. Sephacell) and a solution of an organic solvent (e.g. methanol) at a concentration sufficient to permeablize the hydrophobic membane to water (e.g. about 60% v/v).. After a second incubation period for a time and at a temperature to permite assay-detectable transcript binding (e.g. 0.5 to 1.5 hours at room temperature), the general purpose hand transfers each plate to a vacuum diaphram where the substantially all of the liquid phase is simultaneously filtered from each well. A measured aliquot of wash solution is then added and then vacuum filtered through each well until background counts are reduced to an assay-acceptable level. Optionally, the the bottom of each plate may be blotted onto an absorbent membrane after one or more filtration steps to remove residual liquid from the bottom of each well. The bottom of the drip director of each well is then sealed (e.g. heat melt sealed) and a measured aliquot of scintillation cocktail added to each well. Thereafter, the amount of label retained in each designated well is quantified.

In more preferred embodiments, the pipetting hand is equipped with an 8 or 12 channel pipettor capable of depositing aliquots in at least 8 or 12 wells simultaneously and the multidrop microbead distribution station is capable of filling ninety-six wells simultaneously. Preferred robots are capable of processing at least 640 and preferably at least about 1,280 candidate agents every 24 hours, e.g. in microtiter plates.

The following examples are offered by way of illustration and not by way of limitation.

EXAMPLES

Example 1

Prokaryotic (*E. coli*) RNA Polymerase Assay (Promoter Specific)

In this example, the targeted polymerase is the *E. coli*. RNA polymerase holoenzyme ($\alpha_2\beta\beta'_{94}$) supplemented with additional recombinant sigma 70 to increase the percentage of promoter specific transcription over non-specific elongation. GTP is omitted from the assay mixture. The substrate is a pBR-based plasmid with sigma 70, −10+−30 recognition sequences and a 260 nt G-free cassette 1. Make 1.45× assay buffer from 5× stock (1× final with extract and enzyme added). Add fresh components (polyethyleneglycol (PEG), dithiothreitol (DTT), and DNA) to final 1x solution; 50 mM Tris-Ac at pH 7.8, 100 μm ATP, 100 μM UTP, 1 μM CTP, 20 μg Bovine Serum Albumin/80 μl, PEG 3%, plasmid DNA template (described above), 0.3–0.5 μg/80 μl (from dose response), 2 mM DTT. Filter using 0.45 μm filter.
2. Make 1× storage buffer (50 mM Tris-Ac, 100 mM KAc, 100 mM MgCl2, 0.25 mg/ml BSA, 5 mM DTT). Add enzyme and [Δ-$^{33}$P]-CTP to a concentration such that there are about 80–100K cpm CTP in 15 μl, and enough enzyme (from dose response) to get 3000 cpm incorporated.
3. Add 60 μl of assay buffer to filterplate.
4. Add 8 μl of extract or compounds to filterplate.
5. Add 15 μl of $^{33}$P CTP+enzyme to filterplate. Shake 10 min.
6. Incubate 45 min at 34° C.
7. Add 100 μl of DEAE Sephacell (Pharmacia) beads (20% slurry in 60% methanol, 20 mM EDTA, 0.02% NP-40). Incubate 1 hr.

8. Wash 5 times (300 µl each) with 0.5M dibasic NaPi, 0.5% NP-40, 10% ethanol.

9. Seal bottom, add 160 µl cocktail, seal top, and count.

Exemplary Results

Column 1 of both plate #1 and #2 are background counts. Column 12, rows A and B of both plate #1 and #2 are positive controls using the bacterial RNA polymerase II inhibitor rifampin at 20 ug/ml. All remaining wells received candidate extract or compound: plate #1 received 10 ug extract/compound per well and plate #2 received 30 ug extract/compound per well. Dry extracts/compounds were resuspended or dissolved in DMSO for addition to wells. Filter plates were as described in preferred embodiment above. Extracts D7 and D8 provided approximately 70% inhibition at the low 10 ug concentration.

about 80–100 CK cpm of hot CTP in 15 µl, and enough enzyme (from dose response) to get 3000 cpm incorporated.

3. Add 60 µl of assay buffer to filterplate.

4. Add 8 µl of extract or compounds to filterplate.

5. Add 15 µl hot CTP+enzyme to filterplate. Shake 10 min.

6. Incubate 45 min at 34° C.

7. Add 100 µl of DEAE beads (20% slurry in 60% methanol, 20 mM EDTA, 0.02% NP-40). Incubate 1 hr.

8. Wash 5 times (300 µl each) with 0.5M dibasic NaPi, 0.5% NP-40, 10% ethanol.

| Protocol #: 11 | | | | E. Coli | | | User: | | | | |
|---|---|---|---|---|---|---|---|---|---|---|---|
| Data Mode: | | CPM | | | | | | | | | |
| Radionuclide | | P33 MOD WU | | Scintillator: Liquid | | | Energy Range: High | | | | |
| Efficiency Mode: | | High | | Region A: 1.10–256.80 | | | Region B: 1.10–2.56 | | | | |
| Count Time (min): | | 0.20 | | | | | | | | | |
| Count Termination: | | no | | | | | | | | | |
| Count Delay (min): | | 0.00 | | | | | | | | | |
| Target Temperature: | | 19.0° C. (66.2° F.) | | | | | | | | | |
| Plate Orientation: | | Normal | | | | | | | | | |
| Background Subtract: | | none | | | | | | | | | |
| Half Life Correction: | | no | | | | | | | | | |
| Sample Screening: | | no | | | | | | | | | |
| Quench Indicator: | | tSIS | | | | | | | | | |
| Data File Name: | | ecolidat | | | | Drive & Path: A:\ | | | | | |

| CPM A | 1 | 2 | 3 | 4 | 5 | 6 | 7 | 8 | 9 | 10 | 11 | 12 |
|---|---|---|---|---|---|---|---|---|---|---|---|---|
| | | | | Protocol #: 11 | | Plate #: 1 | Plate ID: 0 | | | | | |
| A | 89.00 | 4287.50 | 4772.00 | 5199.00 | 5061.50 | 5318.50 | 5048.50 | 4281.00 | 5754.00 | 5481.00 | 7043.50 | 605.50 |
| B | 0.00 | 4594.00 | 5418.00 | 3232.00 | 3409.50 | 3097.50 | 2501.50 | 1126.50 | 3811.50 | 5120.50 | 6152.00 | 717.00 |
| C | 147.00 | 5339.50 | 5082.00 | 3848.50 | 3592.50 | 2777.00 | 2236.50 | 2624.50 | 3076.00 | 5095.00 | 5278.50 | 7446.50 |
| D | 291.50 | 5335.50 | 5522.00 | 3098.00 | 3575.00 | 2607.50 | 1360.00 | 1782.00 | 4024.00 | 5948.50 | 5647.00 | 7406.00 |
| E | 10.00 | 5403.00 | 5864.00 | 4183.50 | 2880.50 | 2732.50 | 3038.50 | 2886.00 | 4717.00 | 5429.00 | 6527.00 | 7576.50 |
| F | 49.50 | 5583.00 | 5922.50 | 5601.00 | 3999.50 | 3625.50 | 4139.00 | 2805.50 | 5193.00 | 5538.50 | 5744.00 | 7577.50 |
| G | 89.50 | 5237.50 | 5707.50 | 6271.00 | 5224.50 | 5310.50 | 5832.00 | 5126.00 | 5075.50 | 5002.50 | 5293.50 | 6810.00 |
| H | 49.50 | 4547.00 | 4901.50 | 5251.00 | 5353.00 | 5326.50 | 5552.00 | 3943.00 | 4838.00 | 5419.50 | 5107.50 | 5288.50 |
| | | | | Protocol #: 11 | | Plate #: 2 | Plate ID: | | | | | |
| A | 49.00 | 4924.50 | 4803.00 | 5688.00 | 5429.00 | 4857.00 | 5160.00 | 3176.00 | 4983.00 | 4835.00 | 5034.00 | 578.50 |
| B | 3.00 | 4173.50 | 3942.00 | 3758.50 | 1395.00 | 1806.00 | 1876.00 | 620.00 | 2616.00 | 4189.50 | 4745.50 | 452.50 |
| C | 34.00 | 4635.00 | 3325.00 | 1439.00 | 1050.00 | 1392.50 | 2381.00 | 1498.00 | 1734.00 | 3709.50 | 4707.00 | 7745.50 |
| D | 5.00 | 4322.50 | 5616.00 | 1208.50 | 1482.50 | 1686.50 | 831.00 | 875.00 | 2405.00 | 3317.00 | 4686.00 | 7199.50 |
| E | 14.50 | 5140.50 | 2701.50 | 1428.50 | 1592.50 | 1751.20 | 1544.50 | 3513.50 | 1936.50 | 3606.00 | 4949.50 | 8983.00 |
| F | 10.00 | 5149.20 | 4766.00 | 1801.50 | 1920.50 | 1885.00 | 1500.50 | 1108.00 | 1692.50 | 3019.50 | 3448.00 | 8538.50 |
| G | 0.00 | 5298.00 | 4632.50 | 1938.50 | 1584.50 | 1950.50 | 3317.00 | 1599.50 | 1773.50 | 3956.50 | 4571.00 | 8176.50 |
| H | 3.00 | 3235.00 | 5451.50 | 2123.50 | 2712.50 | 2364.00 | 4004.50 | 1257.00 | 3197.50 | 5082.50 | 4983.50 | 1477.50 |

Example 2

Eukaryotic (Yeast) RNA Polymerase II Assay (Promoter Nonspecific)

1. Make 1.45× assay buffer from 5× stock (1× final with extract and enzyme added). Add fresh components (PEG, DTT, and $MnCl_2$) to final 1× solution: 50 mM Tris-Acetate at pH 7.8, 50 mM KAc, 0.4 mM ATP, 0.2 mM GTP and UTP, 1 µM CTP, 20 µg BSA/80 µl, PEG 3%, single stranded DNA, 0.2 µg/80 µl, 2 mM DTT, and 2 mM $MnCl_2$. Filtrate using 0.45 µm filter.

2. Make 1× storage buffer (50 mM Tris-Ac, 100 mM KAc, 0.25 mg/ml BSA, 5 mM DTT). Add enzyme and [$\alpha$-$^{33}$P]-CTP to a concentration such that there are 9. Seal bottom, add 160 µl cocktail, seal top, and count.

Exemplary Results

Column 1, rows A–D of both plate #1 and #2 are background counts. Column 1, rows E–H of both plate #1 and #2 are counts obtained without the additon of label. Column 12, rows A and B of both plate #1 and #2 are positive controls using the eukaryotic RNA polymerase II inhibitor $\alpha$-amanitin at 20 ug/ml. All remaining wells received candidate natural plant extract: plate #1 received 10 ug extract per well and plate #2 received 30 ug extract per well. Dried extracts were resuspended or dissolved in DMSO for addition to wells. Filter plates were as described in preferred embodiment above. Extracts F4 and F5 provided approximately 80% inhibition—far in excess of that provided by $\alpha$-amanitin—at the low 10 ug concentration.

| | | | | | | | | | | | | |
|---|---|---|---|---|---|---|---|---|---|---|---|---|
| Protocol #: 12 | | | | | | Candida | | | User: | | | |
| Data Mode: | | CPM | | | | | | | | | | |
| Radionuclide | | P33 MOD WU | | | | Scintillator: Liquid | | | Energy Range: High | | | |
| Efficiency Mode: | | High | | | | Region A: 1.10–256.00 | | | Region B: 1.10–2.56 | | | |
| Count Time (min): | | 0.20 | | | | | | | | | | |
| Count Termination: | | no | | | | | | | | | | |
| Count Delay (min): | | 0.00 | | | | | | | | | | |
| Target Temperature: | | 19.0° C. (66.2° F.) | | | | | | | | | | |
| Plate Orientation: | | Normal | | | | | | | | | | |
| Background Subtract: | | none | | | | | | | | | | |
| Half Life Correction: | | no | | | | | | | | | | |
| Sample Screening: | | no | | | | | | | | | | |
| Quench Indicator: | | tSIS | | | | | | | | | | |
| Data File Name: | | candida.dat | | | | Drive & Path: a:\ | | | | | | |

| CPM A | 1 | 2 | 3 | 4 | 5 | 6 | 7 | 8 | 9 | 10 | 11 | 12 |
|---|---|---|---|---|---|---|---|---|---|---|---|---|
| | | | | Protocol #: 12 | Plate #: 1 | Plate ID: 0 | | | | | | |
| A | 946.00 | 14876.5 | 9052.00 | 13657.0 | 5511.00 | 12772.5 | 12392.0 | 12071.0 | 13823.0 | 11605.5 | 1834.50 | 6477.00 |
| B | 932.50 | 15986.5 | 9921.50 | 13187.5 | 11324.0 | 9136.50 | 11366.0 | 12124.0 | 13197.0 | 13677.0 | 13289.5 | 6882.00 |
| C | 780.00 | 13788.0 | 10289.0 | 13983.0 | 12251.5 | 12518.5 | 11315.0 | 12442.5 | 13004.5 | 10693.5 | 13344.5 | 14128.0 |
| D | 1062.00 | 13134.0 | 13452.0 | 12323.0 | 13449.5 | 4940.50 | 10528.0 | 12078.0 | 13148.0 | 11681.5 | 13934.5 | 13575.0 |
| E | 19.50 | 12765.0 | 11491.0 | 12818.0 | 9725.00 | 4182.50 | 13111.0 | 13405.5 | 12518.5 | 4250.00 | 11458.0 | 13825.0 |
| F | 20.00 | 11753.5 | 13143.0 | 2782.00 | 3872.50 | 4958.50 | 12672.0 | 13582.5 | 10858.5 | 13465.0 | 15862.5 | 14371.5 |
| G | 5.00 | 14220.0 | 12488.0 | 8692.00 | 14625.5 | 2409.5 | 12110.5 | 11395.5 | 11088.5 | 12744.0 | 12347.0 | 14882.5 |
| H | 15.00 | 13574.5 | 5355.00 | 14385.0 | 13285.0 | 1240.50 | 12905.5 | 13984.5 | 12810.5 | 12874.5 | 14171.5 | 14538.0 |
| | | | | Protocol #: 12 | Plate #: 2 | Plate ID: 0 | | | | | | |
| A | 757.50 | 15132.0 | 12110.5 | 12677.5 | 9873.0 | 12840.5 | 12682.5 | 12784.0 | 13249.5 | 12514.5 | 3576.50 | 6999.00 |
| B | 725.00 | 13166.5 | 9665.00 | 12969.0 | 12474.0 | 13665.0 | 12031.0 | 13261.5 | 10645.5 | 12901.5 | 13174.5 | 7028.50 |
| C | 585.00 | 13424.0 | 11709.5 | 12907.0 | 13526.5 | 12907.0 | 13208.5 | 12608.0 | 12350.5 | 12792.5 | 12524.0 | 14963.5 |
| D | 669.50 | 13233.0 | 11655.0 | 13046.0 | 13224.5 | 8817.50 | 13798.0 | 12790.5 | 13319.5 | 12864.0 | 13853.0 | 14858.0 |
| E | 5.00 | 11436.5 | 12501.5 | 12409.0 | 11623.0 | 8071.50 | 13323.5 | 13107.0 | 12702.0 | 8957.00 | 12629.5 | 14295.0 |
| F | 14.50 | 12621.5 | 12200.0 | 6133.00 | 6415.00 | 9176.00 | 13226.0 | 14507.5 | 11472.5 | 13018.0 | 13508.5 | 14538.5 |
| G | 19.00 | 14177.5 | 12499.0 | 10991.5 | 14078.5 | 2532.50 | 12297.0 | 13489.5 | 12106.0 | 11623.0 | 12648.0 | 14126.5 |
| H | 18.50 | 13573.0 | 9305.50 | 11929.0 | 14402.0 | 13647.0 | 13169.0 | 13947.0 | 13481.0 | 12456.0 | 13649.5 | 13759.0 |

Example 3

Purification Procedure for Candida Albicans RNA polymerase II 1. 450 g wet weight Candida Albinans cells (Yeast Genetic Stock Center #28367) suspended in 1.5 ml Extraction buffer per gram cells are snap frozen cells in liquid nitrogen.
2. Frozen cells are ground in 200 to 300 ml of liquid nirogen by blending first at low, then medium, then high speed in Waring blender equipt with a stainless steel cup until the liquid nitrogen is evaporated. Repeat six times.
3. Add 1.5 ml Buffer A per gram wet weight of cells. Titrate to 250 mM KCl. Mix until a homogeneous suspension is formed.
4. Centrifuge in SS34 rotor at 13,000 rpm for 45 mm at 4 C. Filter through Whatman 3 MM paper. Combine and freeze pellets.
5. Dilute with Buffer A to 0.1M KCl and apply to a heparin-Sepharose CL6B column (300 ml, 5×7.5 cm). Elute polymerase activity with 0.6M KCl in Buffer A (150 ml).
6. Ammonium sulfate precipitate at 42 g/100 ml.
7. Centrifuge at 13,000 rpm for 45 min in SS34 rotor as described above.
8. Resuspend pellet in Buffer B to 0.5M ammonium sulfate. Pass through a DE52-cellulose column (80 ml) to eliminate endogenous nucleic acids.
9. Dialyze or dilute with Buffer B to 0.12M ammonium sulfate. Load on monoQ column (25 ml). Elute with a 150–600 mM linear gradient ammonium sulfate in Buffer B. Assay 2 ml fractions for 70% alpha-amanatin sensitivity at 100 ug/ml. Pool alpha-amanatin sensitive fraction
10. Desalt with Sephadex G-25 to eliminate endogenous nucleotides (if desired).
11. Quick freeze by submersion in liquid nitrogen and store in aliquots at −70 C.

Buffer A: 50 mM Tris-Cl pH 7.9; 1 mM EDTA; 10 mM sodium pyrophosphate; 10% glycerol; 10 mM NaF; and 0.5 mM DTT and protease inhibitors added just prior to use.

Buffer B: 50 mM Tris-Cl pH 7.9; 1 mM EDTA; 20% glycerol; 10 mM NaF; and 0.5 mM DTT and protease inhibitors added just prior to use.

Protease Inhibitors: 0.5 mM PMSF, 1 mM benzamidine, 0.1 mg/ml bacitracin, 1 ug/ml pepstatin, leupeptin and aprotinin.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of identifying an inhibitor of a nucleic acid polymerase activity, said method comprising the steps of:
    forming a mixture of nucleoside triphosphates, a polynucleotide template, a pathogenic nucleic acid polymerase and a candiate inhibitor of nuleic acid polymerase activity, said at least one of said nucleoside triphosphate comprising a detectable label and said polynucleotide template comprising a nucleotide sequence;

incubating said mixture under conditions whereby, but for the presence of said candidate inhibitor, said polymerase transcribes said polynucleotide template by catalyzing the polymerization of said nucleoside triphosphates into a polynucleotide comprising a nucleotide sequence complementary to that of said polynucleotide template;

contacting said mixture with a polycationic, non-sequence-specific, polynucleotide-selective agent immobilized on polymeric microbeads;

incubating said mixture in the presence of said polymeric microbeads under conditions to selectively bind said polynucleotide to said polynucleotide-selective agent;

separating said polymeric microbeads from said mixture by membrane filtration;

washing said polymeric microbeads substantially free of said nucleoside triphosphate;

detecting the presence or absence of said label on said polymeric microbeads;

wherein the absence of said label on said polymeric microbeads indicates that said candidate inhibitor of polymerase activity is an inhibitor of a pathogenic nucleic acid polymerase activity.

2. A method according to claim 1, wherein said polynucleotide-selective agent immobilized on polymeric microbeads is a suspension of diethylaminoethyl-coated polymeric microbeads.

3. A method according to claim 1, wherein said separating step is performed by vacuum-assisted filtration.

4. A method according to claim 1, wherein said forming step, said separating step and said washing step are performed at least in part in a microtiter plate by a computer-controlled electromechanical robot comprising an axial rotatable arm.

5. A method according to claim 1, wherein said separating and said washing step are performed in a tube having a fluid passage comprising a reservoir portion, a first filter and a second filter, each said first and said second filter extending transversely across said passage, said first filter positioned between said reservoir portion of said passage and said second filter said first filter being changeable from water-impermeable to water-permeable by contacting said first filter with an effective concentration of an organic solvent;

and said second filter being water-permeable and having a maximum pore size less than about 200 um diameter.

6. A method according to claim 1, wherein said polymerase is a bacterial RNA polymerase and said template is double-stranded DNA devoid of one of guanine, cytosine and uracil nucleotides.

7. A method according to claim 1, wherein said polymerase is a eukaryotic RNA polymerase and said template is single-stranded DNA or nicked double stranded DNA.

* * * * *